(12) United States Patent
Ergler et al.

(10) Patent No.: US 10,588,583 B2
(45) Date of Patent: Mar. 17, 2020

(54) X-RAY DETECTOR WITH AN ARRANGEMENT OF A PIXELATED SECOND ELECTRODE AND A SCATTERED RADIATION GRID

(71) Applicant: Siemens Healthcare GmbH, Erlangen (DE)

(72) Inventors: Thorsten Ergler, Erlangen (DE); Edgar Goederer, Forchheim (DE); Bjoern Kreisler, Hausen (DE); Miguel Labayen De Inza, Forchheim (DE); Christian Schroeter, Bamberg (DE); Peter Sievers, Erlangen (DE); Kurt Stadlthanner, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 218 days.

(21) Appl. No.: 15/856,162

(22) Filed: Dec. 28, 2017

(65) Prior Publication Data

US 2018/0199899 A1 Jul. 19, 2018

(30) Foreign Application Priority Data

Jan. 17, 2017 (DE) .................. 10 2017 200 653

(51) Int. Cl.
*A61B 6/00* (2006.01)
*G21K 1/02* (2006.01)

(52) U.S. Cl.
CPC .......... *A61B 6/4291* (2013.01); *A61B 6/4208* (2013.01); *G21K 1/025* (2013.01)

(58) Field of Classification Search
CPC ....... A61B 6/4291; A61B 6/4208; A61B 6/44; A61B 6/4233; A61B 6/032; G21K 1/025
See application file for complete search history.

(56) References Cited

U.S. PATENT DOCUMENTS

| | | | |
|---|---|---|---|
| 5,666,395 A * | 9/1997 | Tsukamoto | A61N 5/103 250/370.09 |
| 6,366,643 B1 * | 4/2002 | Davis | G21K 1/025 378/154 |

(Continued)

FOREIGN PATENT DOCUMENTS

| | | |
|---|---|---|
| DE | 102014201772 A1 | 8/2015 |
| DE | 102014216756 A1 | 2/2016 |
| WO | WO 2017122514 A1 | 7/2017 |

*Primary Examiner* — Christine S. Kim
(74) *Attorney, Agent, or Firm* — Harness, Dickey & Pierce, P.L.C.

(57) ABSTRACT

An X-ray detector includes a stack arrangement with a scattered radiation grid and a planar converter element including a first surface and a second surface. The converter element includes a first electrode embodied on the first surface and a pixelated second electrode with two adjacent first electrode elements. The two adjacent first electrode elements include a first width and a first length and the two adjacent first electrode elements are embodied the second surface opposite the first surface. The scattered radiation grid includes a grid wall with a thickness along the boundary between the two adjacent first electrode elements. The grid wall is arranged to be substantially perpendicular on the first surface and, in a projection, substantially parallel to the direction of incidence of the radiation and to the surface normal of the first surface. The grid wall at least partially overlaps the two adjacent first electrode elements.

24 Claims, 8 Drawing Sheets

(56) References Cited

U.S. PATENT DOCUMENTS

| | | |
|---|---|---|
| 2012/0145912 A1 | 6/2012 | Iwakiri |
| 2014/0341333 A1 | 11/2014 | Wang |
| 2015/0216485 A1 | 8/2015 | Ergler |
| 2016/0377748 A1 | 12/2016 | Samkumura |
| 2018/0267181 A1* | 9/2018 | Ergler .................... A61B 6/035 |
| 2018/0356541 A1* | 12/2018 | Steadman Booker .. G01T 1/161 |

* cited by examiner

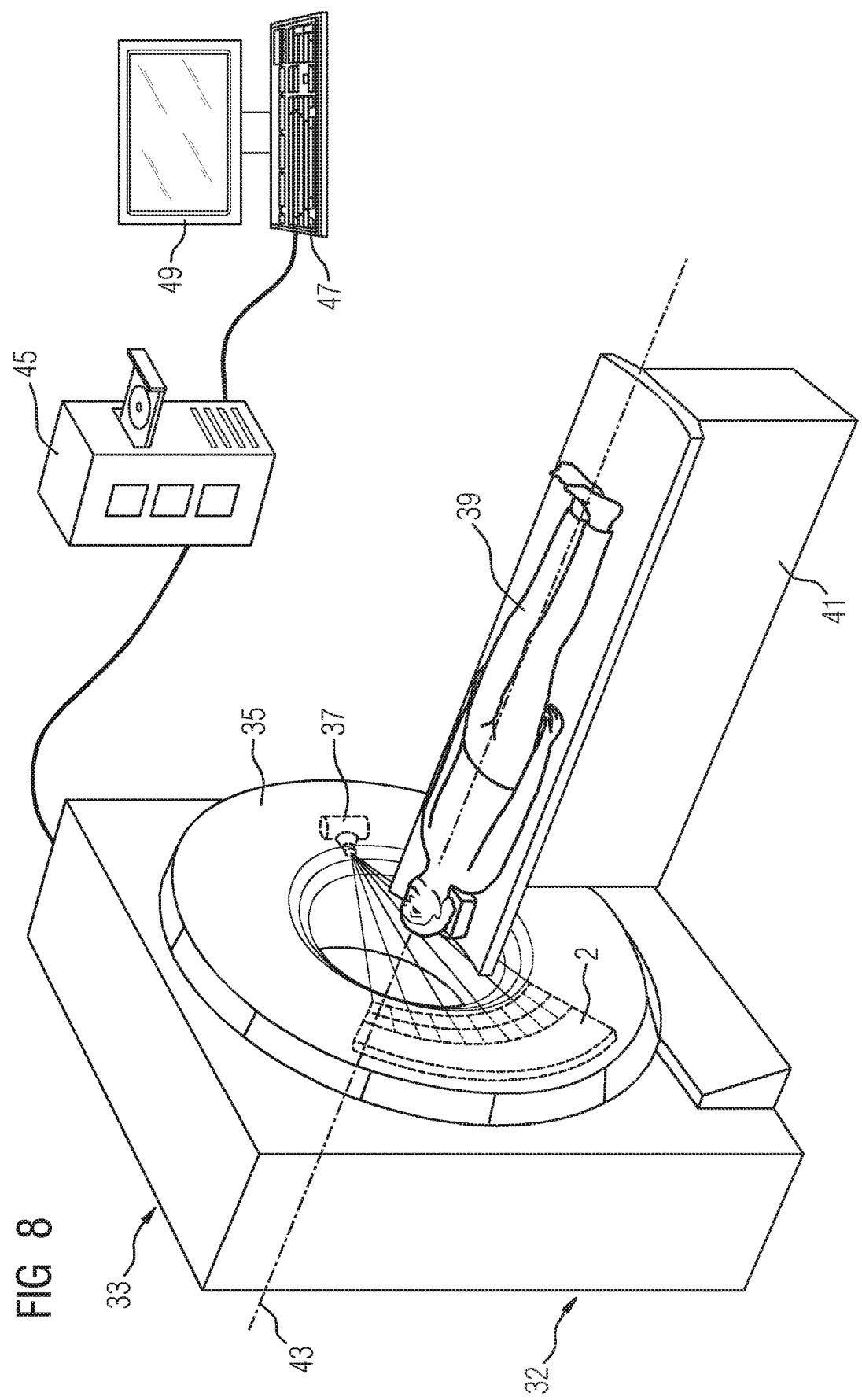

X-RAY DETECTOR WITH AN ARRANGEMENT OF A PIXELATED SECOND ELECTRODE AND A SCATTERED RADIATION GRID

PRIORITY STATEMENT

The present application hereby claims priority under 35 U.S.C. § 119 to German patent application number DE 102017200653.6 filed Jan. 17, 2017, the entire contents of which are hereby incorporated herein by reference.

FIELD

At least one embodiment of the invention generally relates to an X-ray detector with an arrangement of a pixelated second electrode and a scattered radiation grid for increasing signal stability and a medical device for this purpose.

BACKGROUND

Counting direct-conversion X-ray detectors or integrating indirect-conversion X-ray detectors can be used in X-ray imaging, for example in computed tomography, angiography or radiography.

X-rays or photons can be converted into electric pulses in direct-conversion X-ray detectors by way of a suitable converter material. The converter material used can for example be CdTe, CZT, CdZnTeSe, CdTeSe, CdMnTe, InP, TlBr$_2$, HgI$_2$, GaAs, Si or other materials. The electric pulses are evaluated by evaluation electronics, for example an integrated circuit (application specific integrated circuit, ASIC). In counting X-ray detectors, incident X-rays are measured by counting the electric pulses triggered by the absorption of X-ray photons in the converter material. The height of the electric pulse is generally proportional to the energy of the absorbed X-ray photon. This enables the extraction of spectral information from a comparison of the height of the electric pulse with a threshold value. Generally, a scattered radiation grid is embodied on the radiation incidence side of the X-ray detector. The scattered radiation grid suppresses or reduces the detection of the X-ray photons scattered in the object. This enables image artifacts to be reduced.

Known from DE 10 2014 216 756 A1 is a first X-ray projection with a first distribution of first intensity values, which is recorded by an X-ray detector with a plurality of detector elements, wherein these include a collimator and an X-ray source that interacts with the X-ray detector. Each of the first intensity values is assigned to one of the detector elements in each case. A determination of shading of the detector elements by the collimator enables the localization of foci of the first intensity values. Herein, the determination of the shading on the first distribution and the localization step is based on the previously determined shading. Furthermore, each focus is assigned to one of the detector elements in each case.

Known from DE 10 2014 201 772 A1 is a direct-conversion X-ray detector, which comprises a semiconductor used for detecting X-rays. The detector further comprises on the underside, i.e. on the side facing away from the X-rays, a pixelated anode attached to the semiconductor. The anode is divided into a plurality of subpixels. In each case, adjacently arranged subpixels are combined to form a square counting image pixel used for the purpose of detection. Arranged between the image pixels, there is in each case a row of subpixels. These subpixels are not used for detection, i.e. they are non-counting. The non-counting subpixels have an electrically conducting link to one another.

With direct-conversion X-ray detectors, high demands are placed on signal stability. Signal stability can be influenced by different parameters, such as, for example, the temperature, the voltage applied to the converter element, additional lighting and so forth. Signal stability can in particular include the reproducibility of signals or numerical values based on the electric pulses. Signal stability can be influenced by the stability of the focus, for example an X-ray source. An, in particular temporally, unstable focus can influence the shadow-casting by the scattered radiation grid, so that it, for example, changes over time. For example, shadow-casting by the grid wall can change due to an unstable focus such that shading of adjacent detector elements of the grid wall by the grid wall differs over time.

SUMMARY

The inventors have identified that, generally, shadow-casting can influence the electric field in the converter element. A charge or field drift can form in the region of the shadow-casting or the grid walls. The closer the detector element is to the region of the shadow-casting or to a grid wall, the more pronounced the charge or field drift can be.

The inventors have identified that incorrect positioning of the grid wall can result in unwanted shading of a detector element. As a result of mounting tolerances, the grid walls can be, in particular minimally, out of alignment. A precise examination of the beam path of the X-rays reveals that these mounting tolerances for the grid walls result in shading of the active pixel area. The actual shadow can vary if the focus moves. In reality, the focus of the X-ray tube cannot really be aligned in a stable manner and it is not really possible to avoid slight fluctuations in position. These fluctuations cause the shadow-casting by the grid walls, and hence of the signal stability or drift, to change.

The inventors have further identified that the converter element can be subject to so-called radiation drift. If X-rays with a constant photon flux are applied, the output signal of the X-ray detector is not constant over time. The causes of this can be found in the polarization of the converter material. One hypothesis is that impurities in the material are occupied and/or depopulated according to the flux. Even after irradiation with X-rays, polarization effects are still visible for a long period. This signal drift is a major cause of image artifacts. The inventors have identified that, in addition to the grid walls, pixels are subject to particularly strong signal drift.

At least one embodiment of the invention discloses an X-ray detector and/or a medical device that enable increased signal stability or reduced drift.

At least one embodiment of the the invention is directed to an X-ray detector. Further, at least one embodiment of the invention is directed to a medical device.

At least one embodiment of the invention relates to an X-ray detector comprising a stack arrangement with a scattered radiation grid and a planar converter element comprising a first surface and a second surface. The converter element comprises a first electrode embodied on the first surface. The converter element further comprises a pixelated second electrode with two adjacent first electrode elements. The two adjacent first electrode elements, in particular in each case, comprise a first width and a first length. The two adjacent first electrode elements are embodied on the second surface opposite the first surface.

The scattered radiation grid comprises a grid wall with a wall thickness along the boundary between the two adjacent first electrode elements. The grid wall is arranged such that the grid wall is arranged substantially perpendicular on the first surface. The grid wall is further arranged such that, in a projection substantially parallel to the direction of incidence of the radiation and to the surface normal of the first surface, the grid wall at least partially overlaps the two adjacent first electrode elements.

The projection can at least partially overlap each of the two adjacent first electrode elements. In the projection, the grid wall can in particular additionally, at least partially, preferably completely, overlap the interspace arranged between the adjacent first electrode elements.

At least one embodiment of the invention further relates to a medical device comprising an X-ray detector according to at least one embodiment of the invention. The advantages of the X-ray detector according to at least one embodiment of the invention can advantageously be transferred to the medical device according to at least one embodiment of the invention. It is advantageously possible to reduce image artifacts. It is advantageously possible to reduce the influence of fluctuation in the tube focus on image quality. The medical device can preferably be a computed-tomography system.

BRIEF DESCRIPTION OF THE DRAWINGS

The following describes example embodiments of the invention in more detail with reference to drawings, which show:

FIG. 8 a schematic concept of a computed-tomography system according to an embodiment of the invention.

DETAILED DESCRIPTION OF THE EXAMPLE EMBODIMENTS

Figure 1:
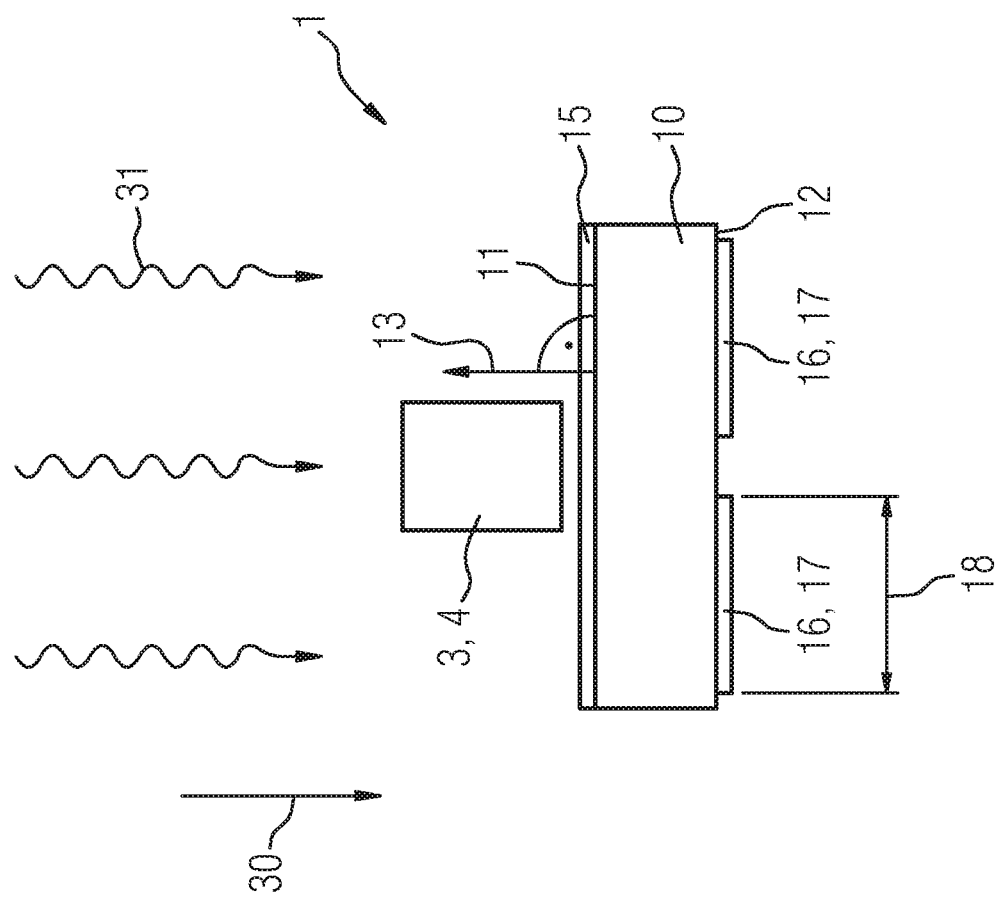
FIG. 1 a schematic concept of an X-ray detector according to the invention according to a first embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an X-ray detector comprising a stack arrangement with a scattered radiation grid and a planar converter element comprising a first surface and a second surface. The converter element comprises a first electrode embodied on the first surface. The converter element further comprises a pixelated second electrode with two adjacent first electrode elements. The two adjacent first electrode elements, in particular in each case, comprise a first width and a first length. The two adjacent first electrode elements are embodied on the second surface opposite the first surface.

The scattered radiation grid comprises a grid wall with a wall thickness along the boundary between the two adjacent first electrode elements. The grid wall is arranged such that the grid wall is arranged substantially perpendicular on the first surface. The grid wall is further arranged such that, in a projection substantially parallel to the direction of incidence of the radiation and to the surface normal of the first surface, the grid wall at least partially overlaps the two adjacent first electrode elements.

The projection can at least partially overlap each of the two adjacent first electrode elements. In the projection, the grid wall can in particular additionally, at least partially, preferably completely, overlap the interspace arranged between the adjacent first electrode elements.

The X-ray detector can in particular be embodied as a direct-conversion X-ray detector. The direct-conversion X-ray detector can comprise at least one detector element per grid cell. The direct-conversion X-ray detector preferably comprises a plurality of detector elements. It can comprise N×M detector elements per grid cell. It is advantageously possible to improve the dose utilization for the imaging. A first electrode element or a possible second electrode element is, for example, assigned to a detector element. The first electrode can preferably be a cathode and the pixelated second electrode an anode. The adjacent first electrode elements can be adjacent first anode elements. The second electrode element can be a second anode element. Alternatively, the first electrode can be an anode and the pixelated second electrode a cathode. The adjacent first electrode elements can be adjacent first cathode elements. The second electrode element can be a second cathode element.

The first electrode and the second electrode can be connected in an electrically conductive manner to the converter element. The first electrode and the second electrode comprise an electrically conductive material. In operation, different potentials are applied to the first electrode and the second electrode so that an electric field forms between the first electrode and the second electrode. The first electrode can be embodied as planar or pixelated. The first electrode can preferably be embodied as planar. The first electrode can have a structure, for example resulting from the method for applying the first electrode to the converter element. The second electrode is pixelated. The second electrode is divided into a plurality of first electrode elements and one possible second electrode element or a plurality of possible second electrode elements. The two adjacent first electrode elements are embodied adjacent to one another. The two adjacent first electrode elements are electrically insulated from one another or not connected to one another directly in an electrically conductive manner. The two adjacent first electrode elements are demarcated from one another. A gap or an interspace is formed as a boundary between the two adjacent first electrode elements between the two adjacent first electrode elements. The first width can preferably be embodied along the direction of rotation of the computed-tomography system. The first length can preferably be embodied along the axis of rotation of the computed-tomography system.

The converter element comprises a first surface and a second surface. The first surface is opposite the second surface. The first electrode is arranged on the first surface. The two adjacent second electrode elements are arranged on the second surface. In operation, the first surface is aligned toward the radiation source. The direction of incidence of the radiation is substantially parallel to the surface normal of the first surface. The second surface is embodied on the surface of the converter element facing away from the radiation source. The first surface be designated the upper side. The second surface can be designated the underside.

The scattered radiation grid can be embodied as a one-, two- or three-dimensional absorber for scattered radiation. The scattered radiation grid is able to absorb scattered X-ray photons in particular, for example in the object to be examined. The scattered radiation grid can preferably be embodied as a three-dimensional absorber with an, for example regular, grid shape. The scattered radiation grid comprises at least one grid wall. The grid wall can in particular be aligned toward a point, for example an X-ray source. The wall thickness can be small compared to the height of the grid wall and/or to the length of the grid wall. The grid wall can preferably be aligned along an interspace or the boundary between the first adjacent electrode elements. In the projection, the grid wall can preferably be embodied along the boundary between the first adjacent electrode elements. Herein, the wall thickness can in particular be embodied perpendicular to the boundary. The boundary can be embodied along the first width or the first length. Along the wall height, which can be embodied along the direction of incidence of the radiation, the wall thickness can be different, for example stepped, or uniform. The grid wall can be arranged substantially perpendicular on the first surface, wherein a difference can be less than 20 degrees, preferably less than 10 degrees and particularly preferably less than 5 degrees.

In particular, when in operational use, the projection is substantially parallel to the direction of incidence of the radiation. The projection is substantially parallel to the surface normal of the first surface. The direction of incidence of the radiation and the surface normal the first surface are substantially parallel. In the projection, the grid wall overlaps the planar extension of the two adjacent first electrode elements at least partially and in particular in each case.

In the projection, the grid wall can additionally at least partially, preferably completely, overlap the interspace arranged between the adjacent first electrode elements along the boundary. In the projection, the grid wall can cover the interspace between the two adjacent first electrode elements, in particular completely.

The inventors have identified that the signal drift can be mainly attributed to a change in the effective pixel size. Since the effective pixel size can be defined by the electrode size of a pixel or the associated field patterns in the converter material itself, it is possible to conclude that the field lines in the converter material are distorted by irradiation with X-rays.

One hypothesis is that the impurity-occupation density in the converter material, and hence the polarization thereof by X-rays, can change. However, no, or virtually no, X-rays arrive at the converter element below the scattered radiation grid. It is possible for a new field distribution to form resulting in a change to the effective pixel size. Detector elements with directly adjacent grid walls can be affected to a greater degree than detector elements that do not have a directly adjacent grid wall. Detector elements with a directly adjacent grid wall on two sides can have the greatest drift effect. Detector elements with only one wall in the immediate vicinity can have a medium drift effect and detector elements without a directly adjacent grid wall have the smallest drift effect. There can be a positive or negative drift.

To date, attempts have been made to configure the dead zone below the grid walls large enough or wide enough for the drift effect to disappear or be greatly reduced. However, it is known that the drift effect has a very long range and extends over a plurality of detector elements. Hence, suppression of the drift effect by dead zones is only very restrictedly possible. A field displacement can result in a change in the effective pixel size. Hence, it is possible for X-ray quanta, which are actually absorbed in the dead zone, i.e. directly next to the grid wall or under the grid wall now to be additionally counted in a counting detector element. The effective pixel size of the detector elements at the edge of a grid wall changes over time and, depending upon the status, captures more or fewer quanta, which is manifested as a drift or change in the counting rate.

The inventors suggest, in at least one embodiment, an arrangement of the second electrode and the scattered radiation grid with which the adjacent first electrode elements extend at least partially within the projection of the grid wall. Hence, in the suggested arrangement, it is advantageously possible to avoid a dead zone or non-counting detector elements.

Advantageously, a pixelated electrode is described in conjunction with a scattered radiation grid, which is able to meet the stability requirements under the boundary conditions of a direct-conversion X-ray detector. It is advantageously possible to minimize negative influences, for example by way of variable shading. It is advantageously possible to minimize signal fluctuations caused by tube fluctuations.

The grid wall itself comprises a wall thickness. For example, the wall thickness can be approximately 100 μm. From a certain planar extension of a detector element, it is now no longer possible for each detector element to be surrounded by, for example, four walls since otherwise, although the patient is exposed to numerous X-ray photons with a dose, due to absorption in the scattered radiation grid, these are not able contribute to the imaging. With the suggested arrangement of the pixelated electrode in conjunction with the scattered radiation grid, it is possible to implement a plurality of electrode elements within a grid cell. Hence, the grid walls enable the dose loss to be kept low or kept constant compared to previous arrangements. With the arrangement of the pixelated electrode in conjunction with the scattered radiation grid, it is advantageously possible to ensure that shading caused by the grid wall conforms to stability requirements.

It is advantageously possible for drift to be reduced with detector elements located in the immediate vicinity of a grid wall. It is advantageously possible to achieve improved clinical images. It is advantageously possible for spatially highly resolved events to be registered in the X-ray detector.

It is advantageously possible to avoid a change in the effective pixel size due to field-line distortions. The field-line distortions can be generated on the outer edge of the pixel by the actual grid wall or by shadow-casting by the grid wall. It is advantageously possible for the influence of focusing instabilities or focusing fluctuations to be reduced.

According to one embodiment of the invention, a second electrode element with a second width and a second length is embodied, in particular completely, outside the projection on the second surface. The second electrode element can, in particular, be not directly adjacent to a grid wall. The second electrode element is not arranged within the projection, which is substantially parallel to the direction of incidence of the radiation and to the surface normal of the first surface. The second electrode element is not arranged below the grid wall. An embodiment with a plurality of second electrode elements is possible. Preferably, all second electrode elements or the effective second pixel size thereof can be of the same size.

Alternatively, an embodiment with second electrode elements with a different size is possible. The second electrode element can be surrounded by a first electrode element so that a detection unit can be formed.

The detection unit can be enclosed by grid walls at least partially, preferably completely. The detection unit can have a sum total of first electrode elements and second electrode elements corresponding to N×M with N,M∈ℕ. The detector elements can, for example, be arranged in N rows and M columns. The detection unit can comprise N×M detector elements. The detection unit can, for example, comprise 1×1, 2×2, 4×4 or 4×6 detector elements. The detector element can be designated as subpixels. The detection unit can be designated as pixels. The detection unit can be made up of subpixels. It is advantageously possible for the influence of the shading with the second electrode elements to be reduced compared to the first electrode elements.

According to one embodiment of the invention, a first planar extension of one of the adjacent first electrode elements is greater than a second planar extension of the second electrode element. The first planar extension can be defined by the area spanned by the first width and the first length. The second planar extension can be defined by the area spanned by the second width and the second length. The planar extension can correspond to the spanned area. The first electrode element is preferably partially, and in particular not completely, arranged within the projection. Within the projection, it is possible for fewer or hardly any X-rays to arrive at the converter element. Hence, the overlapping region of the first electrode element with the projection can make little contribution or no contribution at all to the counting of detected events. In order advantageously to be able to detect the same number of events, the first planar extension can be selected as greater than the second planar extension.

According to one embodiment of the invention, the first width is greater than the second width and/or the first length is greater than the second length. According to one embodiment of the invention, the first width is greater than the second width. The first width of one of the adjacent first electrode elements can be greater than the second width of the second electrode element. The first planar extension can be enlarged compared to the second planar extension by a first width that is greater than the second width. It is advantageously possible for the shading of the second electrode element to be taken into account. The first width and the first length can be different or substantially the same. The second width and the second length can be different or substantially the same.

According to one embodiment of the invention, the first length is greater than the second length. The first length of one of the adjacent first electrode elements can be greater than the second length of the second electrode element. The first planar extension can be enlarged compared to the second planar extension by a first length that is greater than the second length. It is advantageously possible for the shading of the second electrode element to be taken into account.

According to one embodiment of the invention, one of the adjacent first electrode elements comprises a first effective pixel area, which is defined by the gradients of the field lines in regions bounding the adjacent first electrode element and/or the adjacent second electrode element. An effective pixel area can, for example, be determined by the fact that, with homogeneous irradiation of the X-ray detector with X-rays, the counted events are used as a measure for the size of the detector element. The effective pixel area can be determined by the volume assigned to the detector element in the converter element. The volume can be determined by the field lines embodied in the converter element. It is advantageously possible for the detection volume of a detector element or the first electrode element to be defined by gradients of the field lines instead of mechanical separation of the detection volumes from one another. The electric field lines assigned to a detector element can border the electric field lines of the adjacent detector elements.

According to one embodiment of the invention, the second electrode element comprises a second effective pixel area, which is defined by the gradients of the field lines in regions bounding the adjacent first electrode element and/or the adjacent second electrode element. It is advantageously possible for the detection volume of a detector element or the second electrode element to be defined by gradients of the field lines instead of mechanical separation of detection volumes from one another.

According to one embodiment of the invention, the first effective pixel area is defined by shading of incident radiation by the scattered radiation grid. The first effective pixel area of one of the adjacent first electrode elements is defined by shading of incident radiation in operation by the scattered radiation grid. The first effective pixel area can be defined on at least one outer edge or the boundary regions by the shadow-casting by the grid wall. The first effective pixel area can be defined on a further outer edge by the electrode-induced gradients of the field lines. The incidence of X-rays can change the gradients of the field lines, in particular within the projection of the grid wall on the converter element. The field change can advantageously no longer result in a change to the first effective pixel area. The shadow-casting by the grid wall onto the converter element or the detector element can define the active area of the detector element on at least one outer edge of the detector element. The effective pixel area can be reduced by the shading.

According to one embodiment of the invention, the first effective pixel area and the second effective pixel area are substantially the same size. The first effective pixel area of one of the adjacent first electrode elements and the second effective pixel area of the second electrode element can substantially be of equal sizes. The detector elements of a detection unit can preferably have a substantially uniform effective pixel size. It is advantageously possible for the counted events of all detector elements of a detection unit to be equally weighted or compared directly to one another. It is advantageously possible for the detector elements to comprise a uniform effective pixel area. It is advantageously possible to avoid corrections to the first effective pixel area and/or second effective pixel area.

According to one embodiment of the invention, the first effective pixel area and the second effective pixel area are of different sizes. The first effective pixel area of one of the adjacent first electrode elements and the second effective pixel area of the second electrode element are of different sizes. It is advantageously possible for the detector elements of a detection unit to be weighted differently. It is advantageously possible for larger detector elements to acquire more events and be used for example as an estimation of the counting for the detection unit.

According to one embodiment of the invention, the surface area of the first effective pixel area and the surface area of the second effective pixel area differ by a maximum of 30 percent. The surface area of the first effective pixel area of one of the adjacent first electrode elements and the surface area of the second effective pixel area of the second electrode element differ by a maximum of 30 percent. The difference of maximum 30 percent can be compensated by calibration, for example with a spatially homogeneous photon flux and without an object to be examined in the beam path between the radiation source and the X-ray detector. It is advantageously possible to compensate differences in the surface area between different detector elements, for example caused by imprecise positioning of the scattered radiation grid. It is advantageously possible for the signal-to-noise ratio for a plurality of detector elements to be substantially the same. It is advantageously possible to avoid image artifacts. It is also possible to compensate differences of more than 30 percent, but the signal-to-noise ratio can be impaired and so image artifacts can be caused at low counting rates.

According to one embodiment of the invention, the extension of the first effective pixel area along the first width and/or along the first length minus an overlapping region of the first electrode element with the grid wall in the substantially perpendicular projection and the extension of an adjacent second effective pixel area along the second width or along the second length are of equal size. According to one embodiment of the invention, the extension of the first effective pixel area along the first width minus an overlapping region of the first electrode element with the grid wall in the substantially perpendicular projection and the extension of an adjacent second effective pixel area along the second width are of equal size. The grid wall can be arranged such that it at least partially overlaps one of the adjacent first electrode elements in the substantially perpendicular projection. The extension of the first effective pixel area outside the projection along the first width can be the same size as the extension of the second effective pixel area along the second width. It is advantageously possible for the first effective pixel area irradiated by the X-rays to be of the same size as the second effective pixel area irradiated by the X-rays.

According to one embodiment of the invention, the extension of the first effective pixel area along the first length minus an overlapping region of the first electrode element with the grid wall in the substantially perpendicular projection and the extension of an adjacent second effective pixel area along the second length are of equal size. The grid wall can be arranged such that it at least partially overlaps the at least one first electrode element in the substantially perpendicular projection. The extension of the first effective pixel area outside the projection along the first length is of the same size as the extension of the second effective pixel area along the second length. It is advantageously possible for the first effective pixel area irradiated by the X-rays to be the same size as the second effective pixel area irradiated by the X-rays.

According to one embodiment of the invention, an extension of the first effective pixel area and/or the second effective pixel area is based, in particular in each case, on the quotient of an extension of a grid opening of the scattered radiation grid and a joint number of the first electrode elements and the second electrode elements along the extension of the grid opening of the scattered radiation grid. The joint number can correspond to the number of detector elements along the grid opening. The joint number can, for example, correspond to M or N. The extension can designate section, for example along the first width or the first length. In particular, an extension outside the projection equal to the quotient of an extension of a grid opening and the joint number along the extension of the grid opening can be assigned to the first effective pixel area of one of the adjacent first electrode elements. It is advantageously possible for the first effective pixel area irradiated by the X-rays to be the same size as the second effective pixel area irradiated by the X-rays.

According to one embodiment of the invention, an extension of one of the adjacent first electrode elements is based on the sum of the first width or the first length and an extension between two adjacent first electrode elements or between the one adjacent first electrode elements and the adjacent second electrode element. An extension equal to the sum of the first width and the extension between two adjacent first electrode elements can be assigned to one of the adjacent first electrode elements. An extension equal to the sum of the first length and the extension between two adjacent first electrode elements can be assigned to one of the adjacent first electrode elements. An extension equal to the sum of the first width and the extension between the one of the adjacent first electrode elements and the adjacent second electrode element can be assigned to one of the adjacent first electrode elements. An extension equal to the sum of the first length and the extension between two adjacent first electrode elements can be assigned to one of the adjacent first electrode elements. It is advantageously possible for the first effective pixel area to be estimated using the assigned extension.

According to one embodiment of the invention, furthermore a shade-capture structure is arranged between the scattered radiation grid and the converter element. The shade-capture structure comprises an X-ray absorbing material. The shade-capture structure can be produced from the same material as the scattered radiation grid. The shade-capture structure can be embodied in a grid shape. The shade-capture structure and the scattered radiation grid can have mutually matching grid-opening geometry. The wall of the shade-capture structure can be aligned to the focus of the X-ray tube. The wall of the shade-capture structure can in particular be 30 to 100 percent wider than the grid wall. It is advantageously possible for the number of scattered photons registered in the X-ray detector to be reduced. The influence of fluctuations of the tube focus can be reduced.

According to one embodiment of the invention, the X-ray detector further comprises a lighting unit arranged between the scattered radiation grid and the first electrode. It is furthermore possible for a lighting unit for additional lighting of the converter element with infrared, ultraviolet or visible light to be arranged between the scattered radiation grid and the converter element. Preferably, infrared light can be used for the additional lighting. It is advantageously possible for the polarization state of the converter element to be stabilized by way of the additional lighting. In order, for example on the scattered radiation grid, to prevent scattered photons from being registered in the converter element, a shade-capture structure can be arranged below the lighting unit.

At least one embodiment of the invention further relates to a medical device comprising an X-ray detector according to at least one embodiment of the invention. The advantages of the X-ray detector according to at least one embodiment of the invention can advantageously be transferred to the medical device according to at least one embodiment of the invention. It is advantageously possible to reduce image artifacts. It is advantageously possible to reduce the influence of fluctuation in the tube focus on image quality. The medical device can preferably be a computed-tomography system.

FIG. 1 shows an example embodiment of the X-ray detector 1 according to the invention according to a first embodiment in a side view. The X-ray detector 1 comprises a stack arrangement with a scattered radiation grid 3 and a planar converter element 10. The converter element 10 comprises a first surface 11 and a second surface 12. The converter element 10 comprises a first electrode 15 embodied on the first surface 11. The converter element 10 further comprises a pixelated second electrode 16 with two adjacent first electrode elements 16, 17. The two adjacent first electrode elements 16, 17 comprise a first width 18 and a first length. The two adjacent first electrode elements 16, 17 are embodied on a second surface 12 opposite the first surface 11. The scattered radiation grid 3 comprises a grid wall 4 with a wall thickness along the boundary between the two adjacent first electrode elements 16, 17. The grid wall 4 is arranged such that the grid wall 4 is arranged substantially perpendicular on the first surface 11. The grid wall 4 is arranged such that, in a projection that is substantially parallel to the direction of incidence of the radiation 30 and to the surface normal 13 of the first surface 11, the grid wall 4, partially overlaps the two adjacent first electrode elements 16, 17. In operation, X-rays 31 are incident on the X-ray detector 1 along the direction of incidence of the radiation 30.

Figure 2:
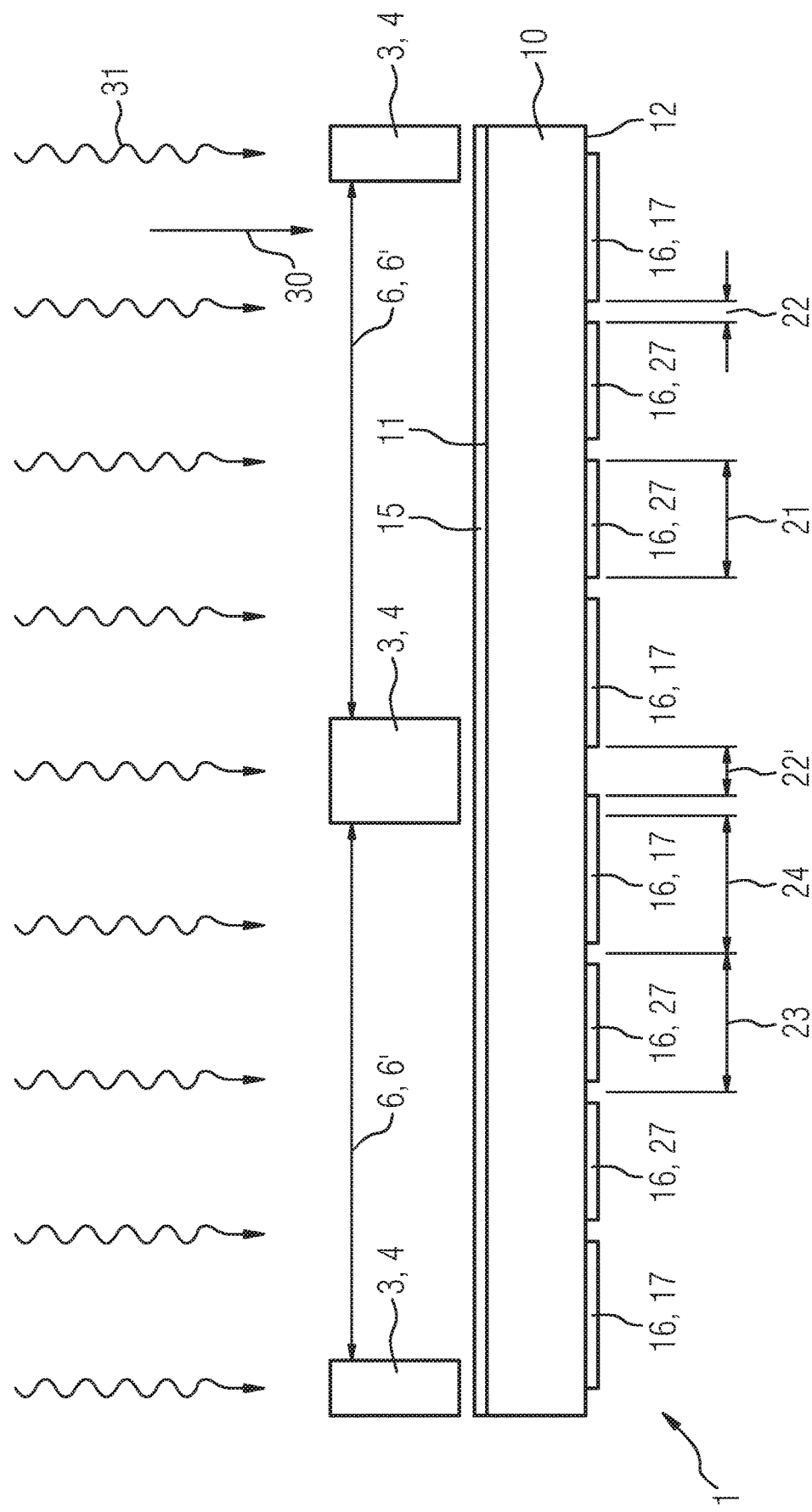
FIG. 2 a schematic concept of an X-ray detector according to the invention according to a second embodiment.

FIG. 2 shows an example embodiment of the X-ray detector 1 according to the invention according to a second embodiment in a side view. The X-ray detector 1 further comprises a second electrode element 16, 27. The second electrode element 16, 27 with a second width and a second length is embodied outside the projection on the second surface 12.

To ensure that the first effective pixel area and the second effective pixel area are substantially the same size, the extension 23 and the extension 24 are selected as substantially the same size. The extensions 21, 22, 22', 23, 24 are arranged along the axis of rotation and/or along the direction of rotation. The respective extensions 21, 22, 22', 23, 24 in the direction of rotation and along the axis of rotation can be selected as different sizes. Herein, the extension 23 is the sum of the extension 21 and the extension 22. The extension 21 is the second width or the second length. The extension 22 is the distance between two adjacent second electrode elements 16, 27 or between an adjacent first electrode element 16, 17 and a second electrode element 16, 27. The extension 22 is 30 to 100 µm. The extension 21 is 100 to 900 µm. The extension 22' designates the distance between two adjacent first electrode elements 16, 17. The extension 22' is preferably 30 to 100 µm or less than 30 µm. The extension 22' is embodied within the projection. The extensions 23, 24 substantially correspond to the quotients of the extension 6, 6' of the grid opening divided by the joint number of the detector elements 17, 27. The two adjacent first electrode elements 16, 17 are electrically isolated from one another.

Figure 3:
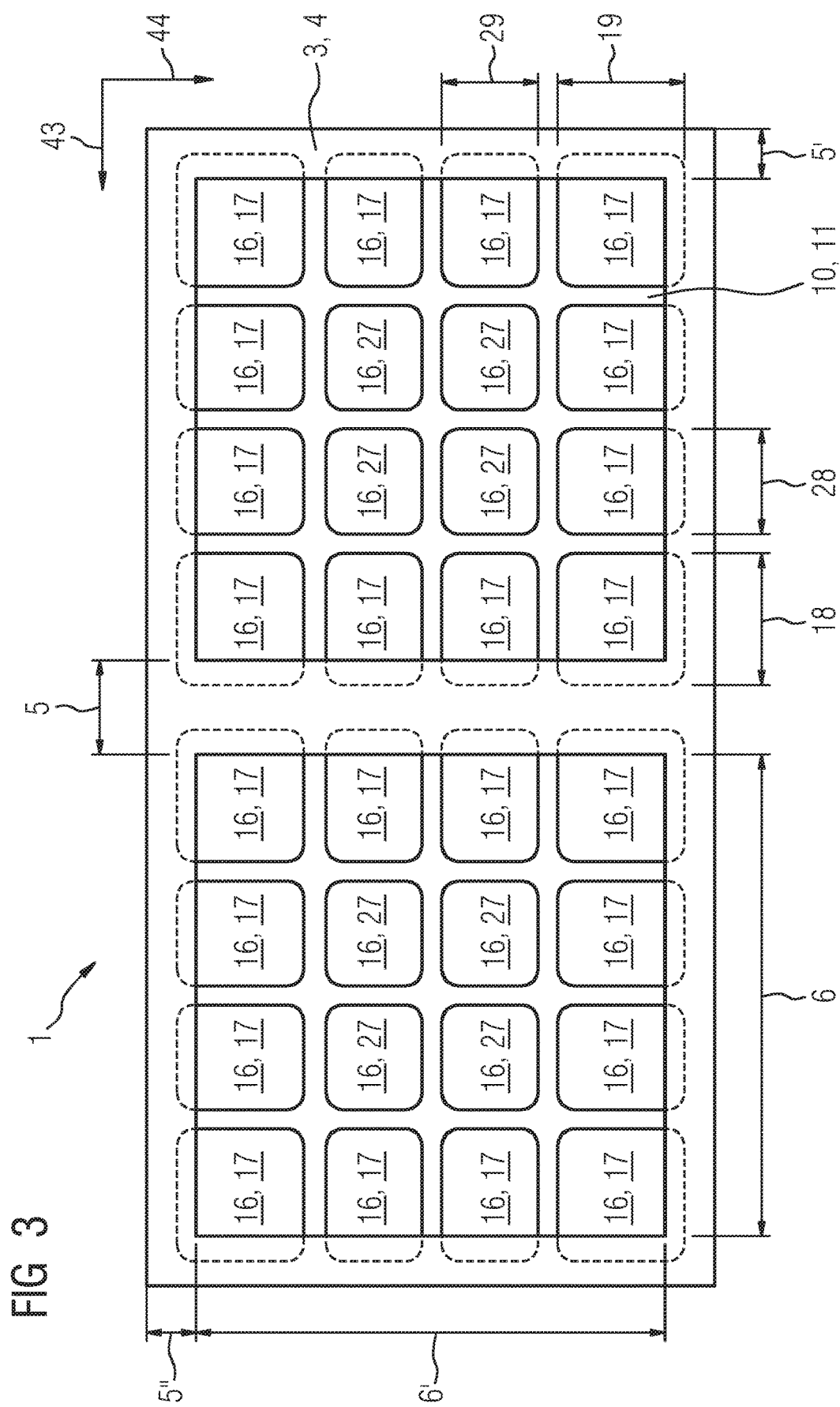
FIG. 3 a schematic concept of an X-ray detector according to the invention according to a third embodiment.

FIG. 3 shows an example embodiment of the X-ray detector 1 according to the invention according to a third embodiment in a top view. The scattered radiation grid 3 is arranged between the radiation source and the converter element 10. The scattered radiation grid 3 is arranged above the first surface 11. The scattered radiation grid 3 comprises an arrangement of grid walls 4 in a substantially rectangular grid arrangement. The grid walls 4 have a wall thickness 5, 5', 5". The wall thickness 5 of an internal grid wall 4 within the scattered radiation grid 3 can have a greater wall thickness 5 than the wall thicknesses 5', 5" of the grid walls 4 at the edge of the scattered radiation grid 3 or the X-ray detector 1. The scattered radiation grid 3 comprises grid openings 6, 6', wherein the extension of the grid opening 6 along the axis of rotation can be the same as or different from the extension of the grid opening 6' along the direction of rotation. The first width 18 and the second width 28 are aligned parallel to the axis of rotation 43. The first length 19 and the second length 29 are aligned parallel to the direction of rotation 44.

The first electrode elements 16, 17 overlap (indicated by dashed lines in FIG. 3) in the projection, which is substantially parallel to the direction of incidence of the radiation and to the surface normal of the first surface 11, partially overlap the grid walls 4. The first electrode elements 16, 17, which partially overlap a grid wall 4 on two sides, have a greater planar extension than first electrode elements 16, 17, which only partially overlap a grid wall 4 on one side. The first electrode elements 16, 17, which partially overlap a grid wall 4 on two sides, all have a substantially same planar extension. The first electrode elements 16, 17, which partially overlap a grid wall 4 on one side only, all have substantially the same planar extension.

The second electrode elements 16, 27 have a substantially identical second width 28 and a substantially identical second length 29. The planar extension of the second electrode elements 16, 27 is substantially constant for all second electrode elements 16, 27. The first width 18 is greater than the second width 28. The first length 19 is greater than the second length 29. For example, the grid opening 6, 6' can correspond to a section 1, wherein the section 1 can, for example, be aligned parallel to the first width 18, second width 28, first length 19 or second length 19. The joint number of the first electrode elements 17 and the second electrode elements 27 can be n with n∈ℕ, for example 4. The extension of the first effective pixel area and/or the second effective pixel area is 1/n, i.e. for example ¼.

Figure 4:
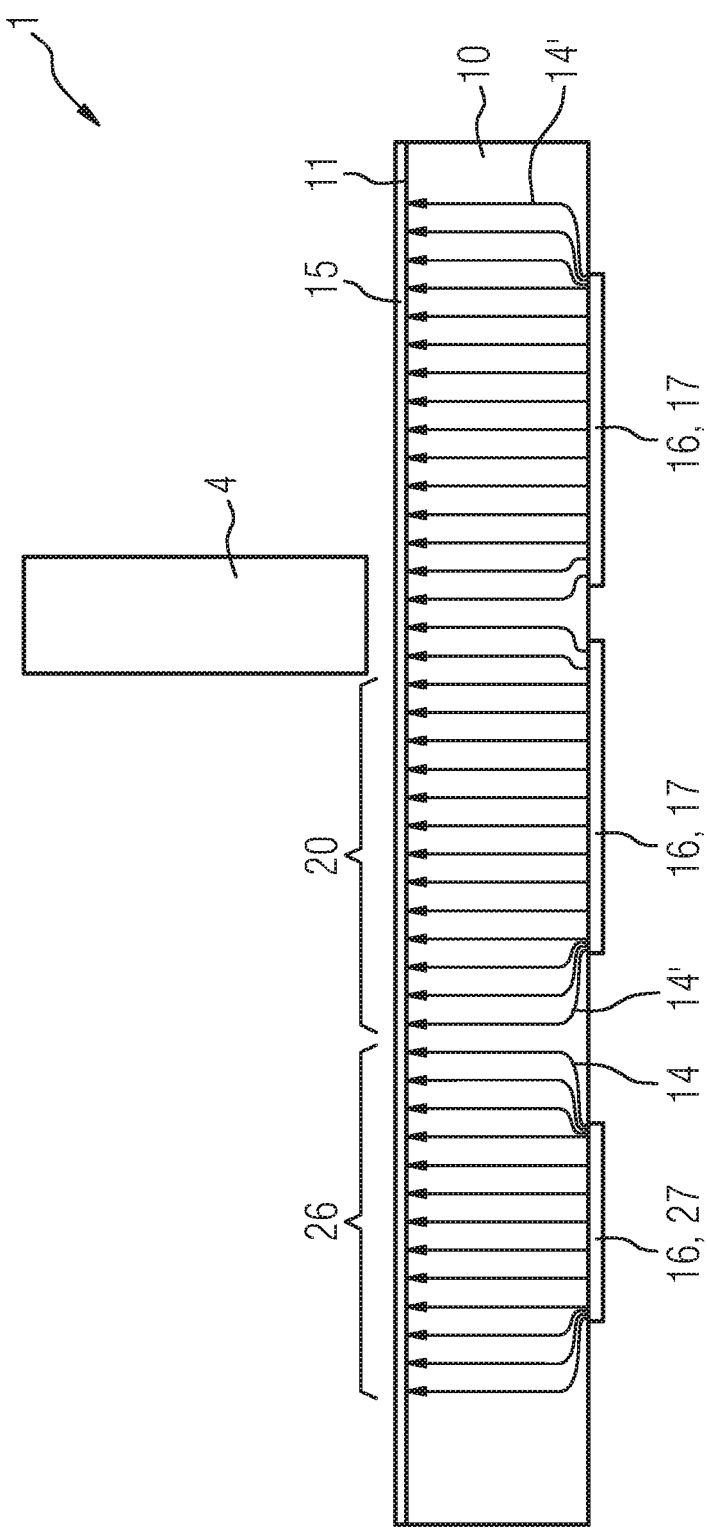
FIG. 4 a schematic concept of an X-ray detector according to the invention according to a fourth embodiment in a first operating state.

FIG. 4 shows an example embodiment of the X-ray detector 1 according to the invention according to a fourth embodiment in a side view in a first operating state. The course of the electric field lines 14 of a second electrode element 16, 27 is shown. The course of the electric field lines 14' of the two adjacent first electrode elements 16, 17 is shown. The electric field lines 14, 14' are depicted in operational state without the influence of X-rays. The field lines 14,14' are substantially embodied uniformly in the converter element 10. The first effective pixel area 20 and the second effective pixel area 26 are substantially the same size.

Figure 5:
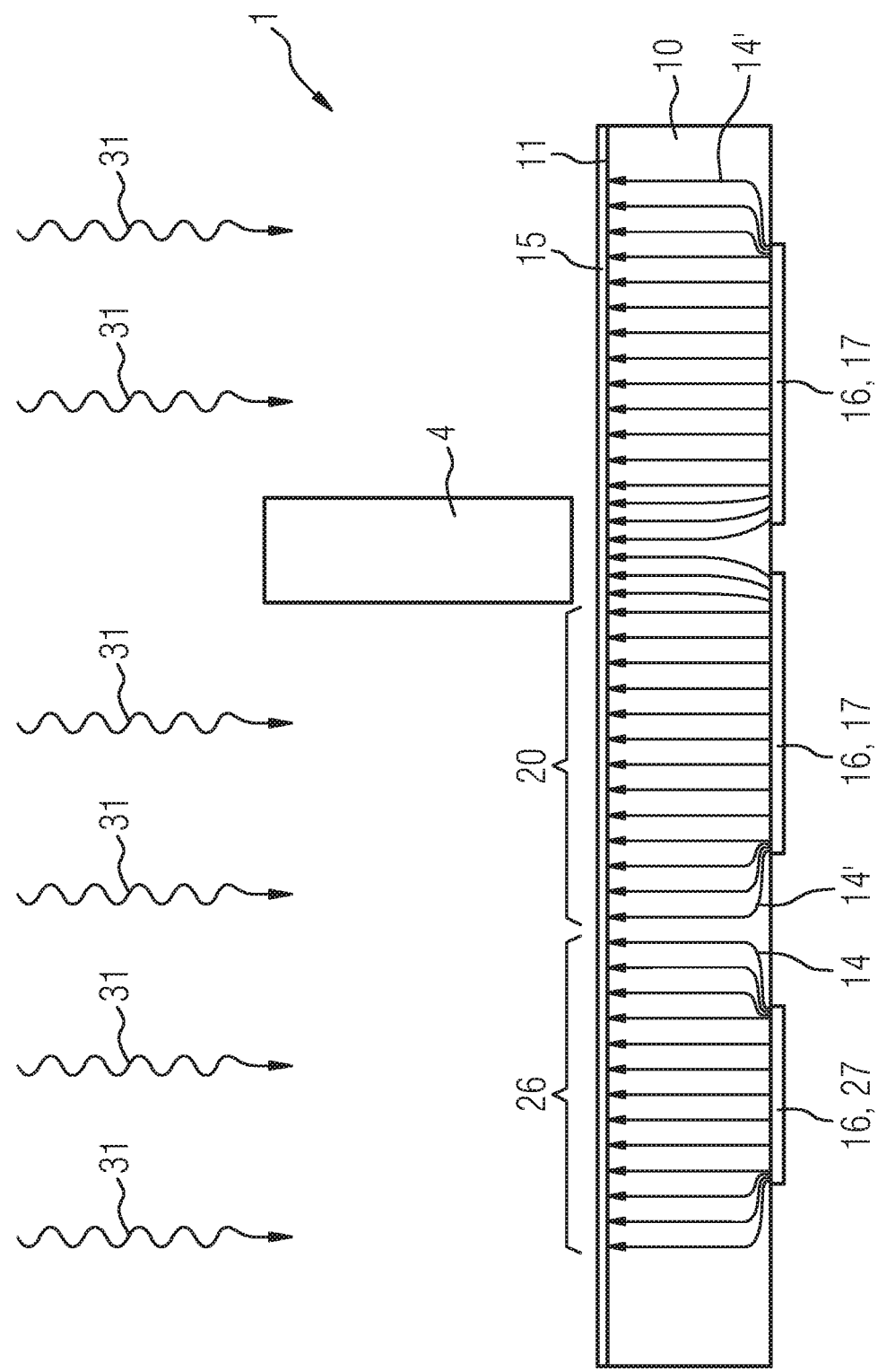
FIG. 5 a schematic concept of an X-ray detector according to the invention according to a fourth embodiment in a second operating state.

FIG. 5 shows an example embodiment of the X-ray detector 1 according to the invention according to a fourth embodiment in a side view in a second operating state. Under the influence of X-rays 31, the field lines 14' toward the boundary between the two adjacent first electrode elements 16, 17 can be changed, distorted or tilted. Under the influence of X-rays 31, the polarization in the converter element 10 can increase and hence the electric field, in particular outside the projection, can decrease so that the electric field within the projection can be intensified. The first effective pixel area 20 and the second effective pixel area 26 are substantially the same size.

Figure 6:
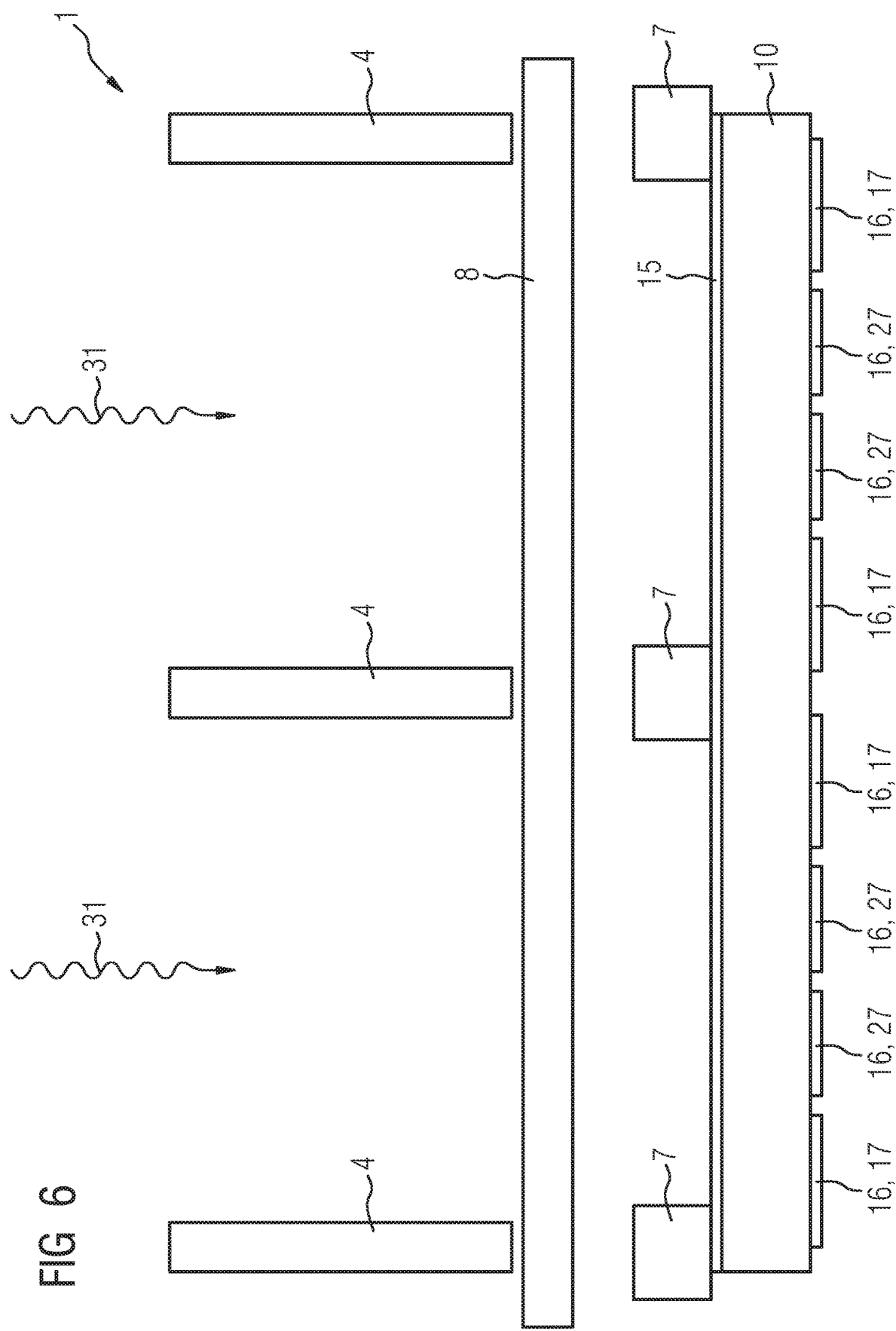
FIG. 6 a schematic concept of an X-ray detector according to the invention according to a fifth embodiment.

FIG. 6 shows an example embodiment of the X-ray detector 1 according to the invention according to a fifth embodiment in a side view. The X-ray detector 1 further comprises a lighting unit 8. The lighting unit 8 is configured to light the converter element 10 with additional, preferably infrared, light. The X-ray detector 1 further comprises a shade-capture structure 7. The shade-capture structure 7 is arranged between the scattered radiation grid with the grid walls 4 and the converter element 10. The shade-capture structure 7 is arranged between the lighting unit 8 and the first electrode 15. The shade-capture structure 7 is preferably arranged in the immediate vicinity of the first electrode 15. The shade-capture structure 7 comprises an X-ray absorbing material. The shade-capture structure 7 preferably comprises the same material as the scattered radiation grid 3. The walls of the shade-capture structure 7 can be embodied wider along the direction of rotation or the axis of rotation than the assigned grid walls 4 of the scattered radiation grid. A wall of the shade-capture structure can be assigned to the grid wall 4, for example in that the grid wall 4 and the wall of the shade-capture structure 7 at least partially overlap in the projection.

Figure 7:
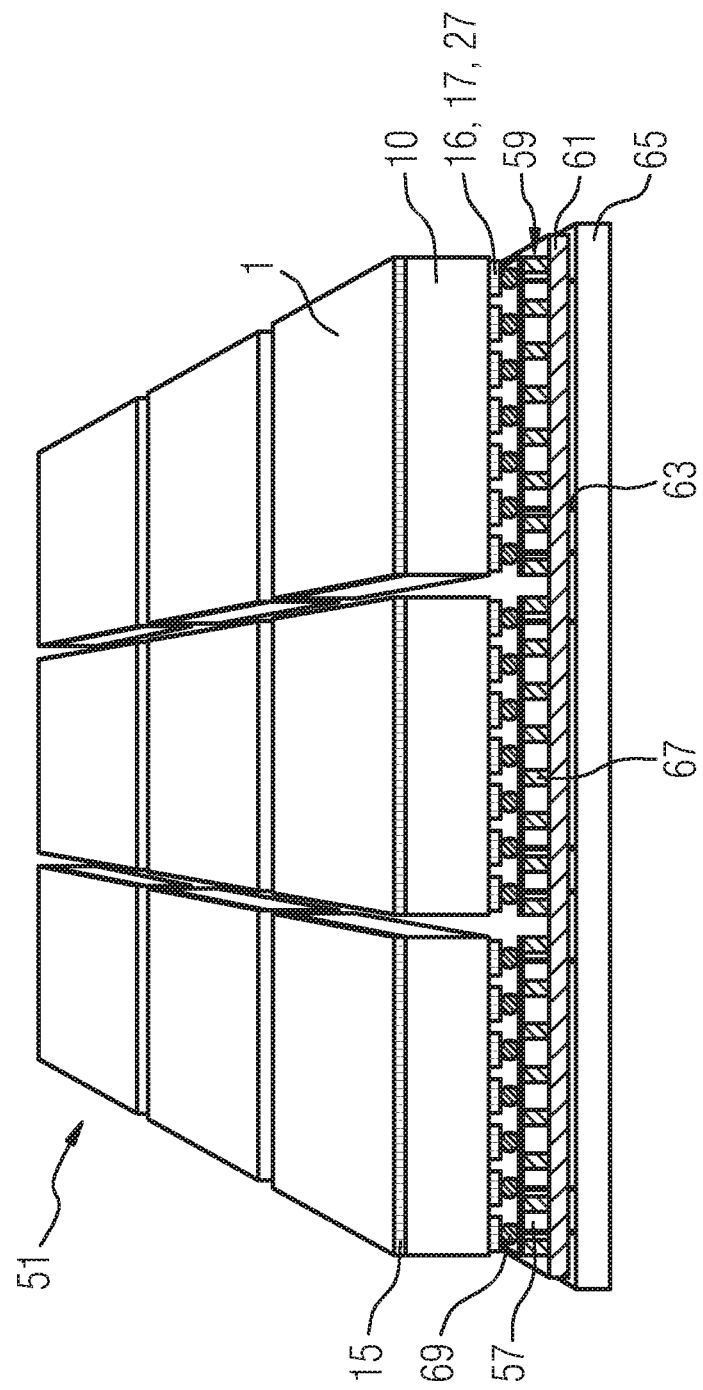
FIG. 7 a schematic concept of a detector module with X-ray detectors according to an embodiment of the invention.

FIG. 7 shows an example embodiment of the detector module 51 with X-ray detectors 1 according to the invention. In a preferred embodiment, the detector module 51 comprises a two-dimensional matrix or arrangement of a plurality of X-ray detectors 1. The number of detector elements can, for example, be within the region ranging from 100 to several thousands. The scattered radiation grid is not shown for reasons of simplicity. The detector elements can comprise a plurality of energy channels. The X-ray detector 1 comprises the converter element 10. The converter element 10 can be embodied as a planar direct converter comprising, for example, CdTe, CZT, CdZnTeSe, CdTeSe, CdMnTe, InP, $TlBr_2$, $HgI_2$, GaAs, Si or other materials as the converter material. The upper side of the converter element 10 comprises a first electrode 15.

The underside of the converter element 10 comprises the second electrode 16, 17, 27. The second electrode 16, 17, 27 is connected via soldered connections 69 to the pixel electrodes 57 and the pixel electronics 67 in the ASIC 59. The soldered connections 69 can, for example, be embodied as bump bonds or solder material in conjunction with copper pillars. The joint number of detection elements 17, 27, the number of soldered connections 69, the number of pixel electrodes 57 and the number of pixel electronics 67 in the ASIC 59 are the same.

The electric field between the first electrode 15 and a detector element 17, 27 determines a sensitive detection volume. The unit comprising a detection volume, a detector element 17, 27, a soldered connect 69, a pixel electrode 57 and pixel electronics 67 connected to the pixel electrode 57 forms a detector element, for example a pixel or subpixel. The ASIC 59 is connected at the underside to a substrate 61. The ASIC 59 is connected via TSV connections 63 running through the substrate 61 to peripheral electronics 65.

FIG. 8 shows an example embodiment of the computed-tomography system 32 according to the invention. The computed-tomography system 32 contains a gantry 33 with a rotor 35. The rotor 35 comprises a radiation source or X-ray source 37 and the detector device 2. The detector device 2 comprises at least one X-ray detector according to the invention. The detector device 2 can comprise a detector module. The object to be examined 39 is supported on the patient bed 41 and can be moved through the gantry 33 along the axis of rotation z 43. A computing unit 45 is used to control and calculate the sectional views. An input device 47 and an output device 49 are connected to the computing unit 45.

Although the invention was illustrated in more detail by the preferred example embodiment, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray detector, comprising
a scattered radiation grid; and
a planar converter element including a first surface and a second surface, the scattered radiation grid and the planar converter element being arranged in a stack arrangement,
the planar converter element including
a first electrode embodied on the first surface,
a pixelated second electrode including two adjacent first electrode elements, wherein the two adjacent first electrode elements include a first width and a first length and wherein the two adjacent first electrode elements are embodied on the second surface opposite the first surface, and
the scattered radiation grid including
a grid wall with a wall thickness along a boundary between the two adjacent first electrode elements, the grid wall being arranged substantially perpendicular on the first surface and, in a projection, substantially parallel to a direction of incidence of radiation and to a surface normal of the first surface, the grid wall at least partially overlapping the two adjacent first electrode elements, wherein a second electrode element with a second width and a second length is embodied on the second surface, outside the projection.

2. The X-ray detector of claim 1, wherein a first planar extension of one of the two adjacent first electrode elements is relatively greater than a second planar extension of the second electrode element.

3. The X-ray detector of claim 2, wherein at least one of the first width is relatively greater than the second width and
the first length is relatively greater than the second length.

4. A medical device comprising:
the X-ray detector of claim 2.

5. The X-ray detector of claim 1, wherein at least one of the first width is relatively greater than the second width and
the first length is relatively greater than the second length.

6. The X-ray detector of claim 1, wherein one of the two adjacent first electrode elements comprises a first effective pixel area, defined by gradients of field lines in regions bounding at least one of an adjacent first electrode element and an adjacent second electrode element.

7. The X-ray detector of claim 6, wherein the second electrode element comprises a second effective pixel area, defined by gradients of field lines in regions bounding at least one of the adjacent first electrode element and the adjacent second electrode element.

8. The X-ray detector of claim 7, wherein the first effective pixel area and the second effective pixel area are of equal size.

9. The X-ray detector of claim 7, wherein the first effective pixel area and the second effective pixel area are of different sizes.

10. The X-ray detector of claim 9, wherein a surface area of the first effective pixel area and a surface area of the second effective pixel area differ by a maximum of 30 percent.

11. The X-ray detector of claim 7, wherein an extension of the first effective pixel area, at least one of along the first width and along the first length, minus an overlapping region of the first electrode element with the grid wall in a substantially perpendicular projection and an extension of an adjacent second effective pixel area along a second width or along a second length, are of equal size.

12. The X-ray detector of claim 7, wherein a first effective pixel area is defined by shading of incident radiation by the scattered radiation grid.

13. The X-ray detector of claim 12, wherein a first effective pixel area and a second effective pixel area are of equal size.

14. The X-ray detector of claim 13, wherein the first effective pixel area and the second effective pixel area are of different sizes.

15. The X-ray detector of claim 6, wherein the first effective pixel area is defined by shading of incident radiation by the scattered radiation grid.

16. The X-ray detector of claim 15, wherein the first effective pixel area and a second effective pixel area are of equal size.

17. The X-ray detector of claim 15, wherein the first effective pixel area and a second effective pixel area are of different sizes.

18. The X-ray detector of claim 6, wherein an extension of at least one of a first effective pixel area and a second effective pixel area is based on a relationship of an extension a grid opening of the scattered radiation grid and a joint number of the two adjacent first electrode elements and the second electrode elements, along the extension of the grid opening of the scattered radiation grid.

19. The X-ray detector of claim 1, wherein an extension of one of the two adjacent first electrode elements is based on a sum of the first width or the first length and an extension between two adjacent first electrode elements or between the one of the two adjacent first electrode elements and an adjacent second electrode element.

20. The X-ray detector of claim 1, wherein a shade-capture structure is arranged between the scattered radiation grid and the planar converter element.

21. The X-ray detector of claim 20, further comprising a lighting unit arranged between the scattered radiation grid and the first electrode.

22. A medical device comprising:
the X-ray detector of claim 21.

23. A medical device comprising:
the X-ray detector of claim 1.

24. The X-ray detector of claim 1, wherein the second electrode element comprises a second effective pixel area, defined by gradients of field lines in regions bounding at least one of the two adjacent first electrode elements and an adjacent second electrode element.

* * * * *